(12) United States Patent
Rezach et al.

(10) Patent No.: US 8,556,904 B2
(45) Date of Patent: Oct. 15, 2013

(54) ANCHORS EXTENDER ASSEMBLIES AND METHODS FOR USING

(75) Inventors: Alan Rezach, Atoka, TN (US); Jason Michael May, Cordova, TN (US)

(73) Assignee: Warsaw orthopedic, Inc., Warsaw, IN (US)

( * ) Notice: Subject to any disclaimer, the term of this patent is extended or adjusted under 35 U.S.C. 154(b) by 95 days.

(21) Appl. No.: 13/101,854

(22) Filed: May 5, 2011

(65) Prior Publication Data
US 2012/0283786 A1 Nov. 8, 2012

(51) Int. Cl.
*A61B 17/70* (2006.01)
(52) U.S. Cl.
USPC ........................................ 606/86 A; 606/305
(58) Field of Classification Search
USPC .......................... 606/247, 279, 99, 104, 86 A
See application file for complete search history.

(56) References Cited

U.S. PATENT DOCUMENTS

| | | |
|---|---|---|
| 4,409,968 A | 10/1983 | Drummond |
| 4,411,259 A | 10/1983 | Drummond |
| 4,877,020 A | 10/1989 | Vich |
| 4,963,144 A | 10/1990 | Huene |
| 5,020,519 A | 6/1991 | Hayes et al. |
| 5,281,223 A | 1/1994 | Ray |
| D346,217 S | 4/1994 | Sparker et al. |
| 5,364,397 A | 11/1994 | Hayes et al. |
| 5,616,143 A | 4/1997 | Schlapfer et al. |
| 5,720,751 A | 2/1998 | Jackson |
| 5,910,141 A | 6/1999 | Morrison et al. |
| 5,941,885 A | 8/1999 | Jackson |
| 6,123,707 A | 9/2000 | Wagner |
| 6,183,472 B1 | 2/2001 | Lutz |
| 6,379,356 B1 | 4/2002 | Jackson |
| 6,648,888 B1 | 11/2003 | Shluzas |
| 6,660,006 B2 | 12/2003 | Markworth et al. |
| 6,726,692 B2 | 4/2004 | Bette |
| 6,730,089 B2 | 5/2004 | Jackson |
| 6,743,231 B1 | 6/2004 | Gray et al. |
| 6,746,449 B2 | 6/2004 | Jones et al. |
| 6,790,208 B2 | 9/2004 | Oribe et al. |
| 7,090,679 B2 | 8/2006 | Saint-Martin et al. |
| 7,156,849 B2 | 1/2007 | Dunbar et al. |
| 7,160,300 B2 | 1/2007 | Jackson |
| 7,179,261 B2 | 2/2007 | Sicvol et al. |
| 7,278,995 B2 | 10/2007 | Nichols et al. |
| 7,341,594 B2 | 3/2008 | Shluzas et al. |
| 7,371,239 B2 | 5/2008 | Dec et al. |
| 7,461,574 B2 | 12/2008 | Lewis et al. |

(Continued)

FOREIGN PATENT DOCUMENTS

| | | |
|---|---|---|
| WO | WO2009/152302 | 12/2009 |
| WO | WO2009/152308 | 12/2009 |

*Primary Examiner* — Eduardo C Robert
*Assistant Examiner* — Lynnsy Schneider (57) ABSTRACT

One nonlimiting embodiment is directed to an anchor extender releasably engaged with an anchor configured for engagement with one or more bones or bony portions. The anchor extender generally includes a first member and a second member positioned about and movable relative to the first member. The anchor extender is positionable adjacent the anchor and movement of the second member relative to the first member toward the anchor as the anchor extender is engaged with the anchor results in lateral displacement of the anchor extender relative to the anchor while the first member engages with a first side of the anchor and the second member engages with an opposite second side of the anchor. However, in other embodiments, different forms and applications are envisioned.

19 Claims, 7 Drawing Sheets

(56) References Cited

U.S. PATENT DOCUMENTS

| | | | |
|---|---|---|---|
| 7,465,306 B2 * | 12/2008 | Pond et al. | 606/86 A |
| 7,470,279 B2 | 12/2008 | Jackson | |
| 7,491,207 B2 | 2/2009 | Keyer et al. | |
| 7,572,281 B2 | 8/2009 | Runco et al. | |
| 7,575,581 B2 | 8/2009 | Lovell | |
| 7,608,081 B2 | 10/2009 | Abdelgany | |
| 7,618,440 B2 | 11/2009 | Gray et al. | |
| 7,618,444 B2 | 11/2009 | Shluzas | |
| 7,621,918 B2 | 11/2009 | Jackson | |
| 7,651,502 B2 | 1/2010 | Jackson | |
| 7,666,189 B2 * | 2/2010 | Gerber et al. | 606/104 |
| 7,713,274 B2 | 5/2010 | Shluzas et al. | |
| 7,758,617 B2 | 7/2010 | Iott et al. | |
| 7,771,430 B2 | 8/2010 | Jones et al. | |
| 7,776,040 B2 | 8/2010 | Markworth et al. | |
| 7,815,650 B2 | 10/2010 | Shluzas et al. | |
| 7,824,411 B2 | 11/2010 | Varieur et al. | |
| 7,824,413 B2 | 11/2010 | Varieur et al. | |
| 7,842,044 B2 | 11/2010 | Runco et al. | |
| 7,909,835 B2 * | 3/2011 | Oribe et al. | 606/104 |
| 7,931,673 B2 * | 4/2011 | Hestad et al. | 606/246 |
| 8,052,720 B2 * | 11/2011 | Kuester et al. | 606/246 |
| 8,096,996 B2 * | 1/2012 | Gutierrez et al. | 606/86 A |
| 8,211,110 B1 * | 7/2012 | Corin et al. | 606/86 A |
| 2003/0225408 A1 | 12/2003 | Nichols et al. | |
| 2004/0034350 A1 | 2/2004 | St. Onge et al. | |
| 2004/0147936 A1 | 7/2004 | Rosenberg et al. | |
| 2004/0147937 A1 | 7/2004 | Dunbar, Jr. et al. | |
| 2004/0249378 A1 | 12/2004 | Saint Martin et al. | |
| 2004/0267275 A1 | 12/2004 | Cournoyer et al. | |
| 2005/0059969 A1 | 3/2005 | McKinley | |
| 2005/0065517 A1 * | 3/2005 | Chin | 606/61 |
| 2005/0149048 A1 | 7/2005 | Leport et al. | |
| 2005/0261702 A1 | 11/2005 | Oribe et al. | |
| 2006/0025768 A1 | 2/2006 | Iott et al. | |
| 2006/0069391 A1 | 3/2006 | Jackson | |
| 2006/0079909 A1 | 4/2006 | Runco et al. | |
| 2006/0089651 A1 | 4/2006 | Trudeau et al. | |
| 2006/0111712 A1 | 5/2006 | Jackson | |
| 2006/0111730 A1 | 5/2006 | Hay | |
| 2006/0149291 A1 | 7/2006 | Selover | |
| 2006/0184178 A1 | 8/2006 | Jackson | |
| 2006/0217735 A1 | 9/2006 | MacDonald et al. | |
| 2006/0247630 A1 | 11/2006 | Iott et al. | |
| 2006/0293680 A1 | 12/2006 | Jackson | |
| 2006/0293692 A1 | 12/2006 | Whipple et al. | |
| 2006/0293693 A1 * | 12/2006 | Farr et al. | 606/104 |
| 2007/0032162 A1 | 2/2007 | Jackson | |
| 2007/0043378 A1 | 2/2007 | Kumar et al. | |
| 2007/0078460 A1 | 4/2007 | Frigg et al. | |
| 2007/0161998 A1 | 7/2007 | Whipple | |
| 2007/0162010 A1 * | 7/2007 | Chao et al. | 606/61 |
| 2007/0233079 A1 | 10/2007 | Fallin et al. | |
| 2007/0260261 A1 | 11/2007 | Runco et al. | |
| 2007/0282337 A1 | 12/2007 | Garamszegi | |
| 2008/0004629 A1 | 1/2008 | Nichols et al. | |
| 2008/0009864 A1 | 1/2008 | Forton et al. | |
| 2008/0015601 A1 | 1/2008 | Castro et al. | |
| 2008/0051794 A1 | 2/2008 | Dec et al. | |
| 2008/0091213 A1 | 4/2008 | Jackson | |
| 2008/0154277 A1 | 6/2008 | Machalk et al. | |
| 2008/0195155 A1 | 8/2008 | Hoffman et al. | |
| 2008/0221626 A1 | 9/2008 | Butters et al. | |
| 2008/0228233 A1 | 9/2008 | Hoffman et al. | |
| 2008/0234678 A1 | 9/2008 | Gutierrez et al. | |
| 2008/0234765 A1 | 9/2008 | Frasier et al. | |
| 2008/0243190 A1 | 10/2008 | Dziedzic et al. | |
| 2008/0288005 A1 | 11/2008 | Jackson | |
| 2009/0018593 A1 | 1/2009 | Barrus et al. | |
| 2009/0030419 A1 | 1/2009 | Runco et al. | |
| 2009/0030420 A1 | 1/2009 | Runco et al. | |
| 2009/0062858 A1 | 3/2009 | Dziedzic et al. | |
| 2009/0082775 A1 | 3/2009 | Altarac et al. | |
| 2009/0088764 A1 | 4/2009 | Stad et al. | |
| 2009/0105712 A1 | 4/2009 | Dauster et al. | |
| 2009/0157125 A1 | 6/2009 | Hoffman et al. | |
| 2009/0171391 A1 | 7/2009 | Hutton et al. | |
| 2009/0228053 A1 | 9/2009 | Kolb et al. | |
| 2009/0228055 A1 * | 9/2009 | Jackson | 606/86 A |
| 2009/0228056 A1 | 9/2009 | Jackson | |
| 2009/0281582 A1 | 11/2009 | Villa et al. | |
| 2009/0318972 A1 | 12/2009 | Jackson | |
| 2009/0318975 A1 | 12/2009 | Abdelgany | |
| 2010/0004696 A1 | 1/2010 | Jackson | |
| 2010/0024487 A1 | 2/2010 | Khoo et al. | |
| 2010/0036434 A1 | 2/2010 | Ely | |
| 2010/0036443 A1 | 2/2010 | Hutton et al. | |
| 2010/0121385 A1 | 5/2010 | Blain et al. | |
| 2010/0137875 A1 | 6/2010 | Marino et al. | |
| 2010/0185242 A1 | 7/2010 | Barry et al. | |
| 2010/0185248 A1 | 7/2010 | Barry et al. | |
| 2010/0228302 A1 | 9/2010 | Dauster et al. | |
| 2010/0249856 A1 | 9/2010 | Iott et al. | |
| 2010/0274252 A1 | 10/2010 | Bottomley et al. | |
| 2010/0292742 A1 | 11/2010 | Stad et al. | |

* cited by examiner

ANCHORS EXTENDER ASSEMBLIES AND METHODS FOR USING

BACKGROUND

The present application relates to surgical devices and methods, and more particularly, but not exclusively, to anchor extender assemblies for use during surgical procedures.

Several surgical procedures utilize anchors that can be secured to bone or bony structures. These anchors can be used to apply stabilizing or corrective forces to the bone or bony structures. A wide variety of anchors are provided that are specifically designed to connect to or engage various bones or bony structures. For example, such anchors can include bone posts or spikes that can be anchored into various bones or bony structures. Additionally, another anchor comprises a hook configured to engage the laminae of the vertebra. Other anchors include spinal screws or bolts having threaded sections configured to be anchored in vertebral bone. With reference to spinal surgery, the anchors are typically used in conjunction with other implant components used to stabilize the vertebra. These other implant components can include, for example, a stabilization device or connecting element such as a spinal rod or plate. Typically, the anchors include a receiver member adapted to engage the connecting element. More particularly, in one form, the receiver member has a channel or opening adapted to receive and engage the connecting element. The receiver member may also be configured to engage a securing member that connects the connecting element to the anchor.

Positioning the connecting element into the channel of the receiver member in-situ can be difficult due to interference with surrounding anatomical features such as skin and soft tissues. Moreover, if the channel of the receiver member is not properly aligned with the connecting element, forces may need to be applied to move the anchor and/or stress the connecting element to achieve proper alignment with the receiver member. Manipulation of the anchor and/or the connecting element can be awkward or cumbersome due to, amongst other things, the limited amount of space available to manipulate the implant components and the required surgical instruments. Thus, there remains a need for further improvements in this area.

SUMMARY

One nonlimiting embodiment of the present application is directed to an anchor extender releasably engaged with an anchor configured for engagement with one or more bones or bony tissues such as, for example, the spinal column. The anchor extender generally includes a first member and second member positioned about and movable relative to the first member. The anchor extender is positionable adjacent to the anchor and movement of the second member relative to the first member toward the anchor as the anchor extender engages the anchor results in lateral displacement of the anchor extender relative to the anchor while the first member engages with a first side of the anchor and the second member engages an opposite second side of the anchor. Amongst other things, the anchor extender can be used for guiding a connecting element, such as a spinal rod, into a receiving channel of the anchor. Moreover, in one non-limiting form, reduction instrumentation can be coupled with the anchor extender and used to reduce the connecting element into the receiving channel of the anchor. Additionally or alternatively, one or more instruments for manipulating the positioning of the anchor may also be coupled with the anchor extender. However, in other embodiments, different forms and applications are envisioned.

For example, another embodiment of the present application is directed to an apparatus that includes an anchor having a bone engaging portion and a receiver member. The receiver member includes a pair of oppositely positioned branches and a receiving channel positioned between the branches and extending between opposite first and second sides of the receiver member. The apparatus also includes an anchor extender engageable with the anchor. The anchor extender includes a first member having an elongate body extending between a proximal end and an opposite distal end and including oppositely positioned first and second arms each having an engaging portion structured to engage a respective one of the branches on the first side of the receiver member. The anchor extender also includes a second member positioned about the first member and movable relative to the first member between a first position and a second position. The second member further includes a distal portion structured to engage the branches on the second side of the receiver member. Distal movement of the second member relative to the first member from the first position to the second position moves the engaging portions of the first and second arms into engagement with the branches on the first side of the receiver member and the distal portion of the second member along the branches on the second side of the receiver member.

In yet another embodiment, an anchor extender includes a first member having a first elongate body extending along a first longitudinal axis between a proximal end and an opposite distal end. The first elongate body also includes a pair of oppositely positioned tabs laterally offset from and extending toward the first longitudinal axis. The anchor extender further includes a second member having a second elongate body extending along a second longitudinal axis between a proximal end and an opposite distal end. The second elongate body includes an elongate passage extending between the proximal and distal ends. The elongate passage includes a first portion positioned adjacent the distal end, a second portion positioned proximally of the first portion, and a transition portion extending obliquely toward the second longitudinal axis in a proximal direction from the first portion to the second portion of the elongate passage. The second member is positionable over the first member and slidably movable relative to the first member across a plurality of positions including an anchor engaging position in which the oppositely positioned tabs are positioned in the elongate passage opposite of and facing the transition portion of the elongate passage.

In another embodiment, a method includes providing an anchor having a bone engaging portion and a receiver member, with the receiver member extending along a central axis between a proximal end and an oppositely positioned distal end and further including a pair of oppositely positioned branches and a receiving channel positioned between the branches. The receiving channel extends between opposite first and second sides of the receiver member. The method also includes providing an anchor extender engageable with the anchor, with the anchor extender extending along a longitudinal axis between a proximal end and an opposite distal end. The anchor extender includes a first member having oppositely positioned first and second arms, each including an engaging portion structured to engage with a respective one of the branches on the first side of the receiver member. The anchor extender also includes a second member movably positioned about the first member and including a distal portion structured to engage the branches on the second side of the receiver member. The method further includes positioning the anchor extender adjacent the proximal end of the receiver member with the longitudinal axis of the anchor extender offset from the central axis of the receiver member, and distally moving the second member relative to the first member to releasably couple the anchor extender with the receiver member. Distally moving the second member relative to the first member includes aligning the longitudinal axis with the central axis.

Another embodiment of the present application is directed to a unique anchor extender for use in surgical procedures in a patient. Other embodiments include unique methods, techniques, systems, devices, kits, assemblies, equipment, and/or apparatus involving anchor extenders.

Further embodiments, forms, features, aspects, benefits, objects and advantages of the present application shall become apparent from the detailed description and figures provided herewith.

DESCRIPTION OF THE ILLUSTRATED EMBODIMENTS

For the purposes of promoting an understanding of the principles of the invention, reference will now be made to the embodiments illustrated in the drawings and specific language will be used to describe the same. It will nevertheless be understood that no limitation of the scope of the invention is thereby intended. Any such alterations and further modifications in the illustrated devices and described methods, and any such further applications of the principles of the invention as illustrated herein are contemplated as would normally occur to one skilled in the art to which the invention relates.

The subject application is generally directed to an anchor extender which can be releasably engaged with an anchor configured for engagement with one or more bones or bony tissues, such as the spinal column, although it should be understood that other skeletal locations are also possible. The anchor extender generally includes a first member and second member positioned about and movable relative to the first member. The anchor extender is positionable adjacent to the anchor and movement of the second member relative to the first member toward the anchor as the anchor extender is engaged with the anchor results in lateral displacement of the anchor extender relative to the anchor while the first member engages a first side of the anchor and the second member engages an opposite second side of the anchor. Amongst other things, the anchor extender can be used for guiding a connecting element, such as a spinal rod, into a receiving channel of the anchor. Moreover, in one non-limiting form, reduction instrumentation can be coupled with the anchor extender, or the anchor extender can be further configured as a reduction instrument, and used to reduce the connecting element into the receiving channel of the anchor. In one or more forms, the anchor extender may also be used to manually manipulate the positioning of the anchor or the bones or bony tissues to which it is engaged. Additionally or alternatively, one or more instruments for manipulating the positioning of the anchor or the bones or bony tissues to which it is engaged may also be coupled with the anchor extender.

Figure 1:
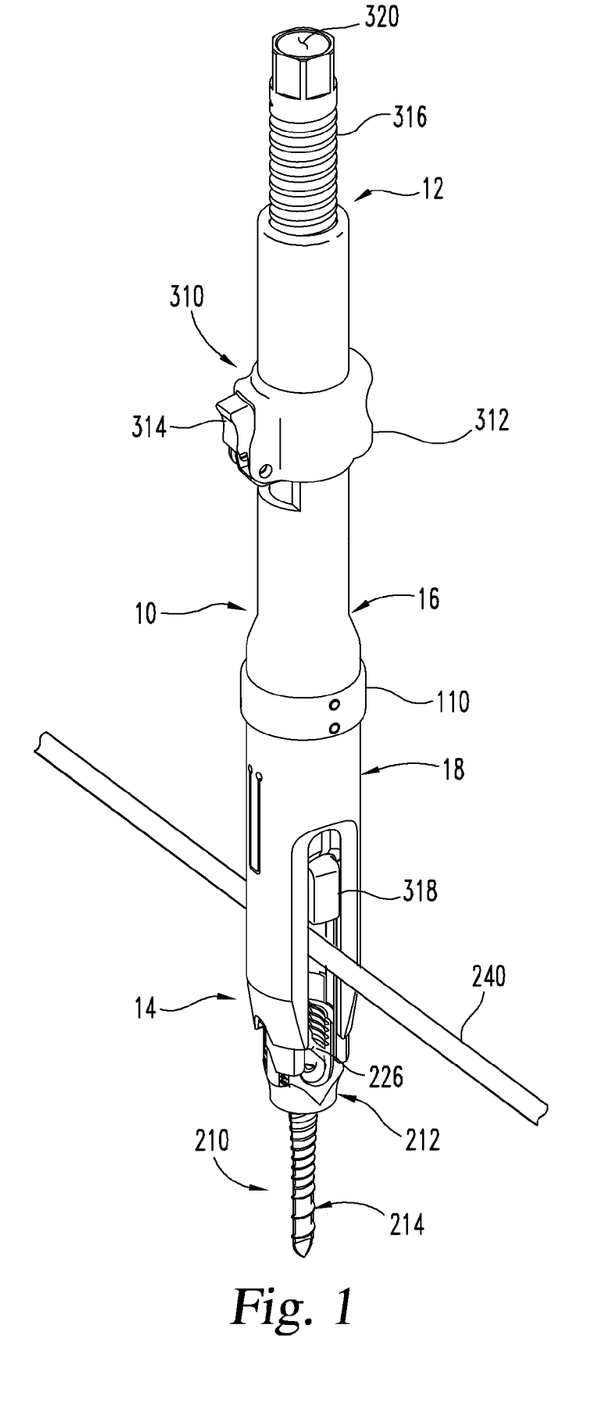
FIG. 1 is a perspective view of an anchor extender positioned in initial engagement with an anchor and to which reduction instrumentation is coupled.
Figure 2:
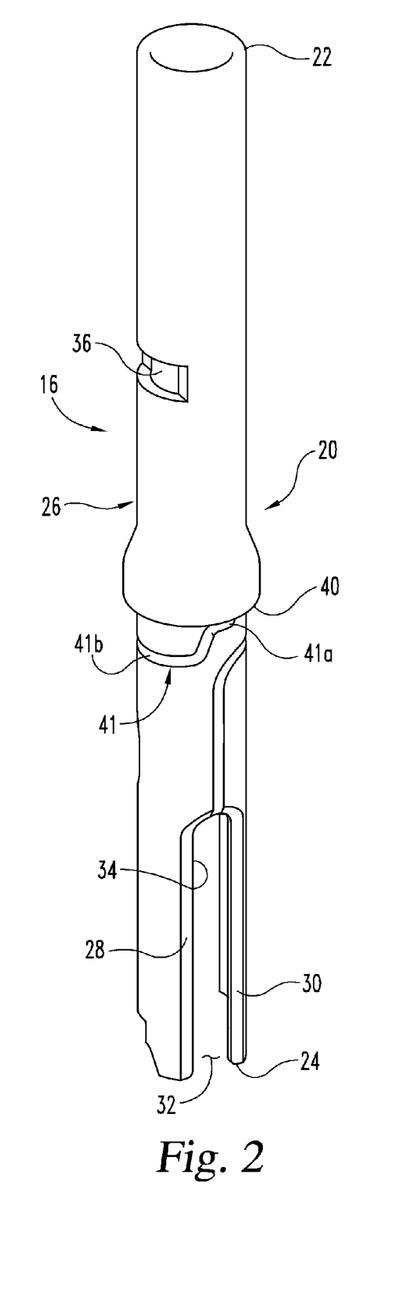
FIG. 2 is a perspective view of a first member of the anchor extender illustrated in FIG. 1.
Figure 8:
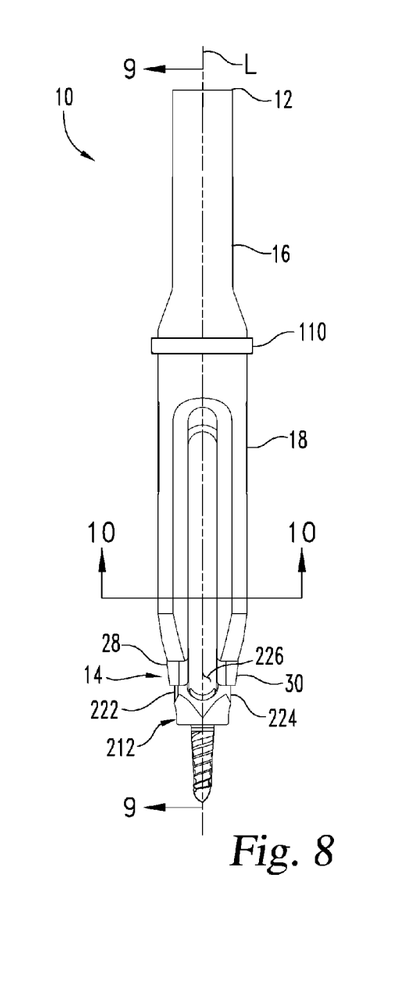
FIG. 8 is a side plan view of the anchor extender illustrated in FIG. 1 positioned in initial engagement with an anchor.
Figure 9:
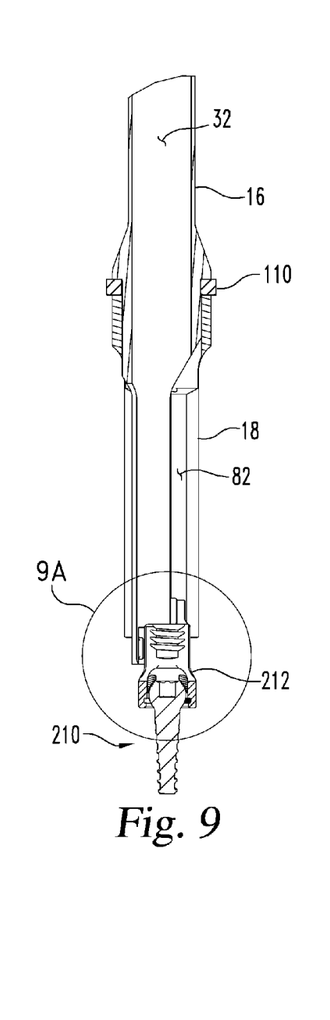
FIG. 9 is an elongate section view of the anchor extender taken along line 9-9 of FIG. 8.
Figure 9A:
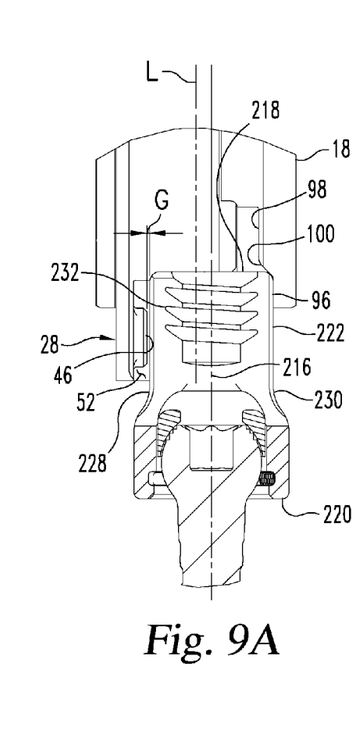
FIG. 9A is an enlarged view of the distal portion of the section view of the anchor extender illustrated in FIG. 9.
Figure 12:
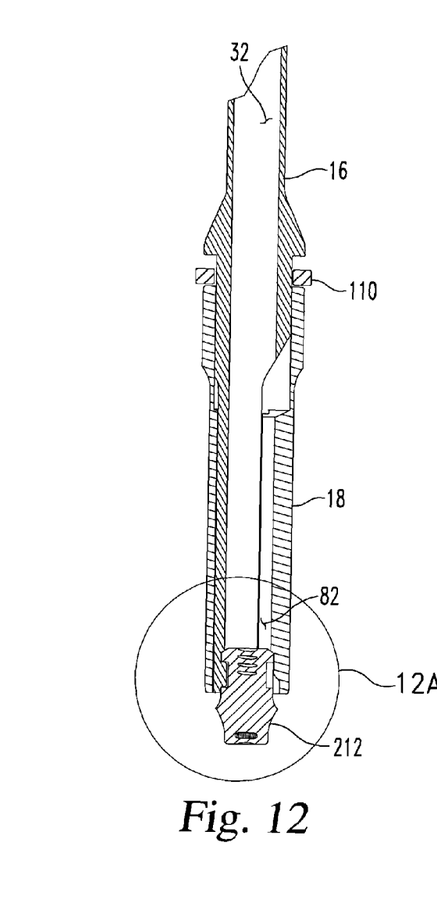
FIG. 12 is an elongate section view of the anchor extender taken along line 12-12 of FIG. 11.
Figure 12A:
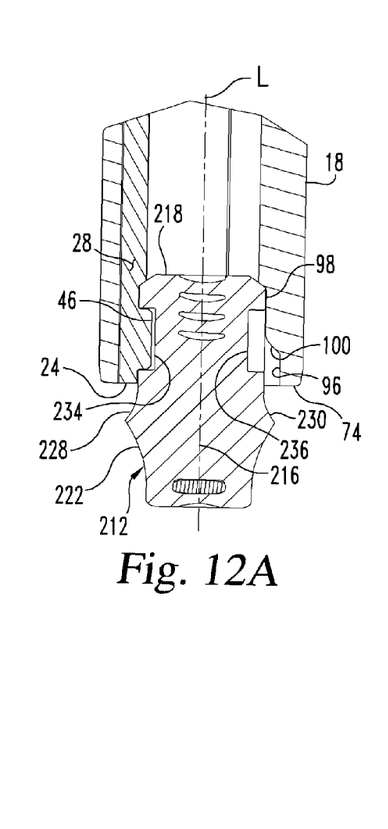
FIG. 12A is an enlarged view of the distal portion of the section view of the anchor extender illustrated in FIG. 12.

Referring now to FIG. 1, there is shown an anchor extender 10 positioned adjacent to a bone anchor 210 and to which reduction instrumentation 310 is coupled, further details of which will be provided below. The bone anchor 210 includes a receiver member 212 configured to receive a connecting element 240 and a distal bone engaging portion 214. While not shown, it should be appreciated that the connecting element can extend between and be coupled with one or more additional anchors configured to be engaged with bones or bony tissues adjacent to the anchor 10. In the illustrated embodiment, the bone engaging portion 214 is a bone screw with a threaded shank structured to engage the bony structure of an underlying vertebra when the bone anchor 210 is engaged to the spinal column. With reference to FIGS. 8 and 9A, the receiver member 212 extends along a central axis 216 between a proximal end 218 and a distal end 220 and includes a pair of opposing branches 222, 224 defining a channel 226 extending between and opening through opposite first and second sides 228, 230 of the receiver member 212. The branches 222, 224 further define a proximal/distally extending opening that opens through the proximal end 218 of the receiver member 212 to receive a set screw (not shown) structured to engage with internal threading 232 on the branches 222, 224 to secure the connecting element 240 in the channel 226. As illustrated in FIG. 12A, the branch 222 includes a pair of oppositely positioned and laterally facing receptacles 234, 236, each of which is configured for individual engagement with a portion of the anchor extender 10 depending on the orientation of the anchor extender 10 relative to the anchor 210, further details of which will be provided below. Additionally, while not illustrated, it should be appreciated that the branch 224 also includes a pair of oppositely positioned and laterally facing receptacles configured the same as the receptacles 234, 236 of the branch 222. In another non-illustrated form, the branches 222, 224 may each include a single lateral facing receptacle positioned on the same side of the receiver member 212.

In the illustrated form, the bone engaging portion 214 is pivotally received in the receiver member 212 through a distal opening thereof, and structured to interact therewith to provide the anchor 210 with multi-axial capabilities that permit either a selected number of positions or infinitely numbered of positions of the bone engaging portion 212 relative to the receiver member 212. Other forms for the anchor 210 are contemplated, including uni-axial and uni-planar forms. The bone engaging portion 214 can also be in the form of a spike, staple, hook, fusion device, cannulated screw, fenestrated screw, interbody device, intrabody device, clamp, plate, suture anchor, bolt, pin or other bone engaging member. The receiver member 214 can also be in the form of a saddle, yoke, eye-bolt or through-hole, side opening member, bottom opening member, top-opening member, eyelet, or any other structure engageable to the connecting element 240 and the anchor extender 10.

In one non-limiting form in which the receiver member 214 is in the form of a side opening member, it includes a proximal branch and an oppositely positioned distal branch which cooperate to define a laterally opening channel that also extends between and opens through opposite first and second sides of the receiver member. In a further aspect of this form, the distal branch can be provided with an opening configured to receive a bone engaging portion in a multi-axial or uni-axial configuration, although forms in which the receiver member and bone engaging portion are integrally formed are also possible. Additionally, the proximal branch can also be provided with a threaded aperture configured to receive and engage with a set screw to secure a connecting element in the laterally opening channel. One non-limiting example of a bone anchor including a laterally opening channel is used in the TSRH® SILO™ Spinal System commercially available from Medtronic Spinal and Biologics, 2600 Sofamor Danek Drive, Memphis, Tenn., 38132. However, it should be understood that other bone anchors including laterally opening channels are also possible. It should also be understood that use of the anchor extender 10 with a bone anchor including a laterally opening channel for receiving the connecting element 240 may be carried out in a manner substantially similar to that discussed below in connection with the use of the anchor extender 10 with the illustrated bone anchor 210.

In the illustrated embodiment, the connecting element 240 is a rigid rod that has a substantially linear configuration between its ends. However, it is contemplated that the connecting element 240 can have a curvature that extends along a constant arc, a varying arc, and/or is compounded between its ends. Additionally, in other forms, the connecting element 240 can include any known configuration for a rod, implant, or fastener. It is further contemplated that the connecting element 240 can be non-rigid, elastic and/or super-elastic and in the form of a cable, band, wire, or artificial ligament that is used in tethering or guiding, and/or in other surgical procedures, It should also be appreciated that other forms in which the anchor extender 10 is used in the absence of the connecting element 240 are also contemplated.

Referring collectively to FIGS. 1 and 8, the anchor extender 10 generally extends along a longitudinal axis L between a proximal end 12 and an opposite distal end 14 which is configured for engagement with the anchor 210, further details of which will be provided below. The anchor extender 10 also includes a first member 16 and a second member 18 positioned about and slidably movable relative to the first member 16. Referring collectively to FIGS. 2-4A, further details of the first member 16 will be provided. The first member 16 includes an elongate body 20 that extends along longitudinal axis L between a proximal end 22 and an opposite distal end 24. The elongate body 20 includes a proximal portion 26 from which first and second spaced apart arms 28, 30 extend, and also including an outwardly flared or tapered portion 38 that defines a distal facing surface 40. A groove 41 is formed in the elongate body 20 adjacent to the distal facing surface 40 and includes a proximal portion 41a and a distal portion 41b. The distal facing surface 40 and the groove 41 are generally configured to cooperate and engage with a collar member coupled with the second member 18, further details of which will be provided below. In the illustrated form, the elongate body 20 generally has a substantially rigid or inflexible configuration such that movement or flexing of the arms 28, 30 relative to one another and/or the proximal portion 26 will be substantially or entirely eliminated. However, it should be appreciated that forms in which the elongate body 20 has a flexible configuration that facilitates movement or flexing of the arms 28, 30 relative to one another and/or the proximal portion 26 are also possible.

Figure 4:
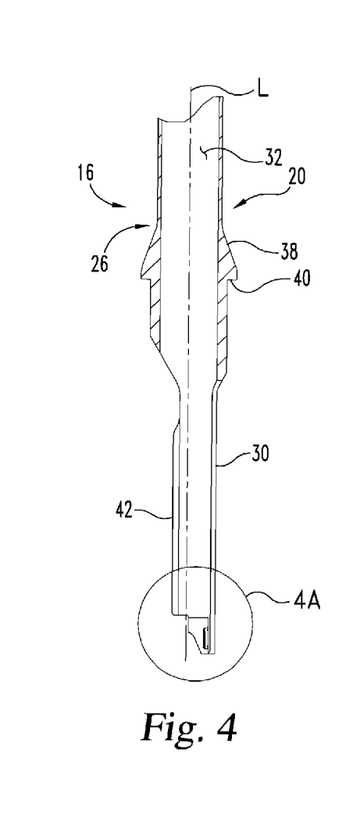
FIG. 4 is an elongate section view of the first member of FIG. 3 taken along line 4-4 of FIG. 3.
Figure 10:
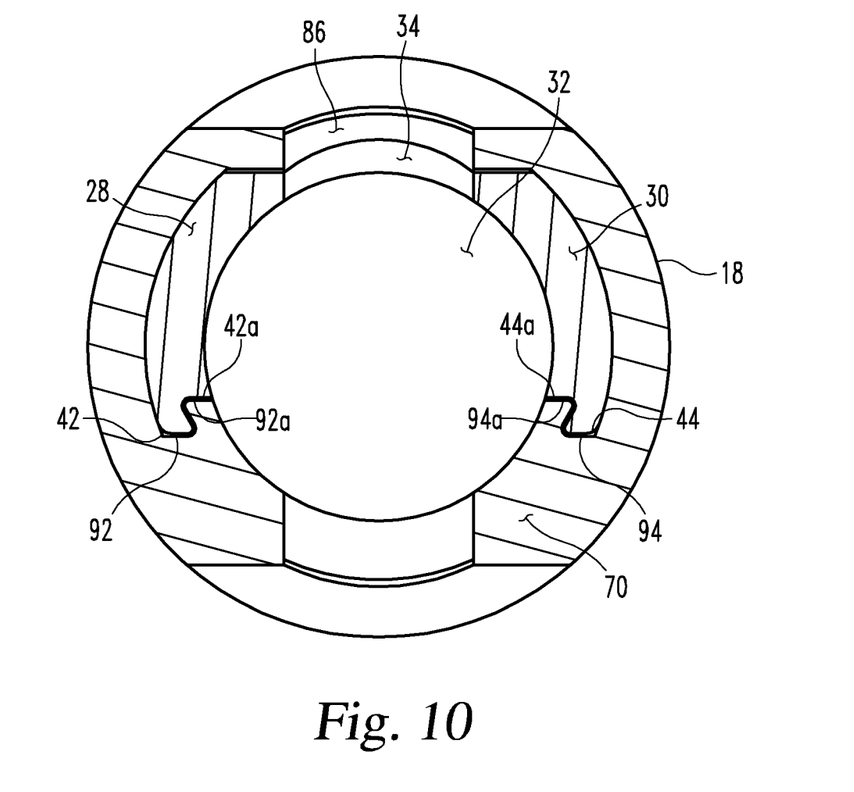
FIG. 10 is a section view of the anchor extender taken along line 10-10 of FIG. 8.

As best seen in FIG. 4, an elongate passage 32 extends through the elongate body 20 from the proximal end 22 to the distal end 24. Additionally, a distally opening elongated slot 34 is positioned between the arms 28, 30 and communicates with the elongate passage 32. The first member 16 also includes an opening 36 that communicates with the elongate passage 32 and is configured to cooperate with the reduction instrumentation 310 when coupled with the anchor extender 10, further details of which will be provided below. The arm 28 also includes a longitudinal tongue 42 positioned adjacent a longitudinal recess 42a (FIG. 10), and the arm 30 includes a longitudinal tongue 44 positioned adjacent a longitudinal recess 44a (FIG. 10). As illustrated in FIG. 10, the longitudinal tongues 42, 44 and recesses 42a, 44a are generally configured to engage with corresponding structure(s) on the second member 18.

Figure 3:
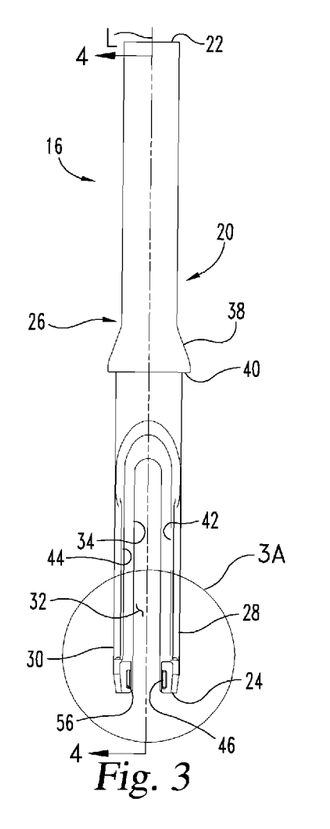
FIG. 3 is a side plan view of the first member illustrated in FIG. 2.
Figure 3A:
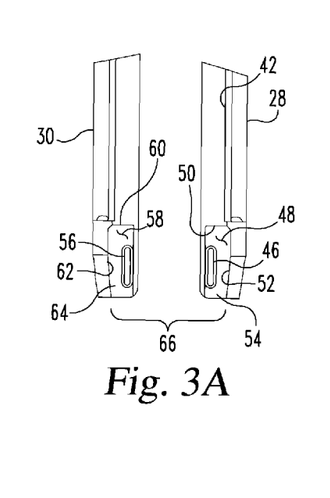
FIG. 3A is an enlarged view of the distal portion of the first member illustrated in FIG. 3.
Figure 4A:
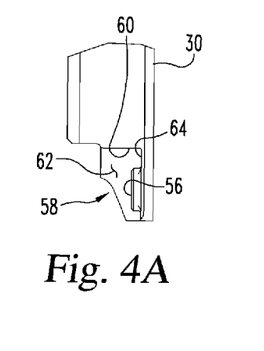
FIG. 4A is an enlarged view of the distal portion of the section view of the first member illustrated in FIG. 4.

The arms 28, 30 each include an engaging portion adjacent the distal end 24 of the elongate body 20 configured to engage the receiver member 212 of the anchor 210. More particularly, with reference to FIG. 3A, the arm 28 includes an engaging portion having an elongate tab 46 positioned in a recess 48 defined by a distal facing surface 50, a side surface 52, and an intermediate surface 54 from which the elongate tab 46 extends. As illustrated in FIGS. 3A and 4A, the arm 30 includes an engaging portion having an elongate tab 56 positioned in a recess 58 defined by a distal facing surface 60, a side surface 62, and an intermediate surface 64 from which the elongate tab 56 extends. The elongate tabs 46, 56 are generally configured to be received in and engage with a respective one of the laterally facing receptacles on the branches 222, 224 on a single side of the receiver member 212. As illustrated in FIGS. 3 and 4, the elongate tabs 46, 56 are positioned on opposite sides of and laterally offset from the longitudinal axis L, and extend substantially parallel with one another away from the arms 28, 30 toward the longitudinal axis L. While not previously discussed, it should be appreciated that the recesses 48, 58 cooperate to define a socket 66 (FIG. 3A) configured to receive a portion of the branches 222, 224 of the receiver member 212, further details of which will be provided below in connection with FIGS. 8-9A and 11-12A.

Figure 5:
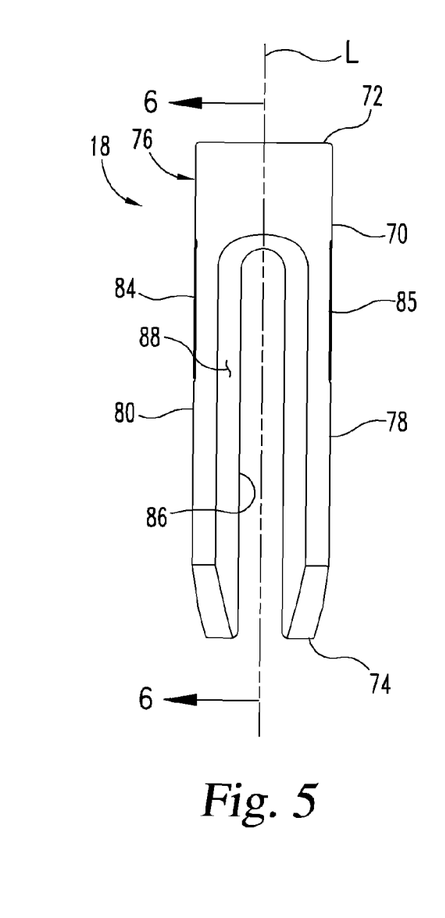
FIG. 5 is a side plan view of a second member of the anchor extender illustrated in FIG. 1.
Figure 6:
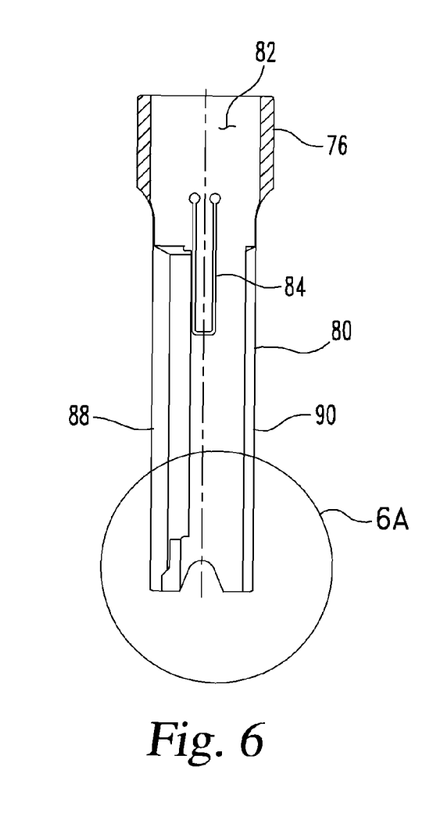
FIG. 6 is an elongate section view of the second member of FIG. 5 taken along line 6-6 of FIG. 5.

As illustrated in FIG. 5, the second member 18 includes an elongate body 70 that extends along longitudinal axis L between a proximal end 72 and an opposite distal end 74. The elongate body 70 further includes a proximal portion 76 from which first and second arms 78, 80 spaced apart from one another and positioned on opposite sides of the longitudinal axis L extend. As illustrated in FIG. 6, an elongate passage 82 extends through the elongate body 70 from the proximal end 72 to the distal end 74 and is configured to receive a portion of the first member 16 therein. Additionally, a distally opening elongated slot 86 is positioned between the arms 78, 80 and communicates with the elongate passage 82. The elongate body 70 also includes a pair of oppositely positioned guide surfaces 88, 90 positioned adjacent opposite sides of the elongated slot 86 and extending obliquely to the longitudinal axis L. The guide surfaces 88, 90 can assist in guiding the connecting element 240 into the elongated slot 86. As illustrated in FIG. 10, the elongate body 70 also includes a pair of internally positioned longitudinal recesses 92, 94 positioned opposite one another and configured to engage the longitudinal tongues 42, 44, respectively, of the arms 28, 30. The elongate body 70 also includes a pair of longitudinal tongues 92a, 94a positioned adjacent the longitudinal recesses 92, 94 and configured to engage with the longitudinal recesses 42a, 44a, respectively, of the arms 28, 30. In this arrangement, the first and second members 16, 18 cooperate with one another to prevent splaying of the arms 28, 30. However, in other non-illustrated forms, the first and second members 16, 18 may alternatively be arranged and provided without any anti-splay arrangement.

Figure 6A:
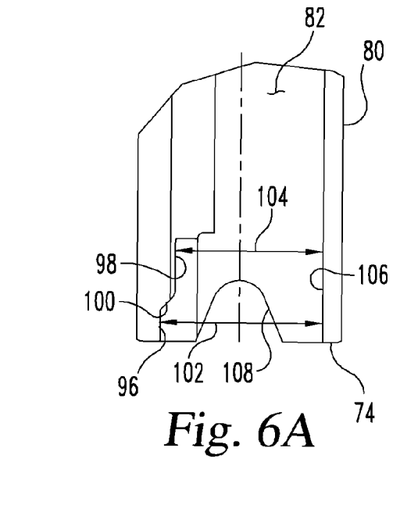
FIG. 6A is an enlarged view of the distal portion of the section view of the second member illustrated in FIG. 6.

The elongate passage 82 opens through the distal end 74 and generally provides a receptacle configured to receive a portion of the receiver member 212 therein. More particularly, as illustrated in FIG. 6A, the elongate passage 82 includes a first portion 96 positioned adjacent to distal end 74 and a second portion 98 positioned proximal the first portion 96. A transition portion 100 extends between the first and second portions 96, 98 and obliquely toward the longitudinal axis L in a proximal direction. In this arrangement, the first portion 96 of the elongate passage 82 includes a first cross-sectional dimension 102 that is greater than a second cross-sectional dimension 104 of the second portion 98 of the elongate passage 82. The elongate passage 82 also includes a generally linear surface 106 positioned opposite the transition portion 100. While the details of the elongate passage 82 adjacent to the distal end 74 of the elongate body 70 have been described in connection with the illustration of the arm 80 in FIGS. 6 and 6A, it should also be appreciated that the foregoing features of the elongate passage 82 are also present in connection with the arm 78, which is configured similar to the arm 80.

The elongate body 70 also includes a pair of oppositely positioned spring tabs 84, 85 configured to engage with or bear against the first member 16 when positioned in the elongate passage 82. Additionally, in the illustrated form, the arm 80 includes an arcuate notch 108 extending proximally from the distal end 74. Moreover, while not illustrated, it should be appreciated that the arm 78 also includes an arcuate notch extending proximally from the distal end 74 and positioned opposite the arcuate notch 108. As indicated above, the second member 18 is positionable over the first member 16. In this arrangement, the first and second arms 28, 30 of the first member 16 are positioned in the elongate passage 82 between the transition portion 100 and the linear surface 106 such that the elongated tabs 46, 56 are generally positioned opposite of and extend toward the transition portion 100.

Figure 7:
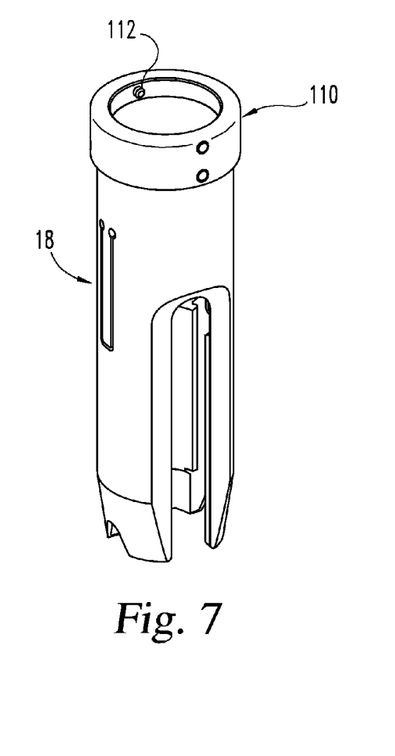
FIG. 7 is a perspective view of the second member of the anchor extender illustrated in FIG. 1 including a collar member coupled therewith.

While not illustrated in FIGS. 5-6A, it should be appreciated that a collar member 110 may be coupled with the proximal end 72 of the elongate body 70 of the second member 18, as illustrated in FIGS. 1 and 7. It should also be appreciated that forms in which the collar member 110 is absent from the anchor extender 10 are contemplated. The collar member 110 is rotatably coupled with the elongate body 70 such that it can be rotated relative to the second member 18. Moreover, the collar member 110 includes an inwardly extending pin 112 engageable within the groove 41 on the first member 16 when the second member 18 is positioned over the first member 16. In this arrangement, the second member 18 can be moved distally from a first position relative to the first member 16 where the pin 112 is positioned in the proximal portion 41a of the groove 41 and the collar member 110 abuts the distal facing surface 40 by rotating the collar member 110 relative to the second member 18. As the collar member 110 is rotated, the pin 112 is distally guided into the distal portion 41b of the groove 41, which in turn results in distal displacement of the second member 18 to a second position relative to the first member 16. Once the second member 18 is in the second position relative to the first member 16, the collar member 110 can be rotated in an opposite direction such that the pin 112 is proximally guided into the proximal portion 41a of the groove 41, and the second member 18 is proximally returned to its first position relative to the first member 16. In another non-illustrated form, the collar member 110 includes internal threads configured to engage with external threads on the first member 16 such that the interaction between the internal and external threads results in proximal and distal displacement of the second member 18 relative to the first member 16 as the collar member 110 is rotated in opposite directions relative to the first member 16.

Referring collectively to FIGS. 8-9A and 11-12A, further details regarding engagement of the anchor extender 10 with the anchor 210 will be provided. More specifically, when the second member 18 is positioned in its first or proximal position relative to the first member 16, the distal end 14 of the anchor extender 10 may be positioned adjacent to the receiver member 212 such that the anchor extender 10 is initially engaged therewith. More particularly, the anchor extender 10 is positionable relative to the anchor 210 such that a portion of the receiver member 212 is positioned in the elongate passage 82. As illustrated in FIG. 9A, in this arrangement, a proximal portion of the branch 222 is positioned in the first portion 96 of the elongate passage 82 such that the proximal end 218 of the receiver member 212 is positioned in abutment against the transition portion 100 and the second member 18 engages the branch 222 on the second side 230 of the receiver member 212. The branch 222 is further positioned between the first arm 28 and the second member 18. Additionally, the arm 28 is positioned adjacent to the first side 228 of the receiver member 212 such that the elongate tab 46 faces the lateral receptacle 234 of the branch 222. However, as illustrated in FIG. 9A, a gap G is positioned between the elongate tab 46 and the first side 228 of the receiver member 212 along the branch 222. A portion of the branch 222 is also received in the recess 48 such that a portion of the side surface 52 extends along an external surface of the branch 222 between the opposite first and second sides 228, 230 of the receiver member 212.

While not illustrated in FIG. 9A, it should be appreciated that a portion of the branch 224 of the receiver member 212 is positioned in the elongate passage 82 and relative to the arm 30 and the second member 18 in the same manner as discussed above in connection with the branch 222. More specifically, a proximal portion of the branch 224 is positioned in the first portion 96 of the elongate passage 82 such that the proximal end 218 of the receiver member 212 is positioned in abutment against the transition portion 100, and the second member 18 engages the branch 224 on the second side 230 of the receiver member 212. The branch 224 is further positioned between the second arm 30 and the second member 18. Additionally, the arm 30 is positioned adjacent the first side 228 of the receiver member 212 such that the elongate tab 56 faces the lateral receptacle (not shown) of the branch 224. However, a gap will also extend between the elongate tab 56 and the first side 228 of the receiver member 212 along the branch 224. A portion of the branch 224 is also received in the recess 58 such that a portion of the side surface 62 extends along an external surface of the branch 224 between the opposite first and second sides 228, 230 of the receiver member 212.

In view of the foregoing, it should be appreciated that the anchor extender 10 can be initially or provisionally engaged with the anchor 210 such that a portion of the branches 222, 224 on the first side 228 of the receiver member 212 are positioned in the socket 66 defined by the arms 28, 30, and a portion of the branches 222, 224 on the second side 230 of the receiver member 212 are positioned in the elongate passage 82. Additionally, as illustrated in FIG. 9A, the longitudinal axis L of the anchor extender 10 is laterally offset from the central axis 216 of the receiver member 212 when the anchor extender 10 is initially engaged with the anchor 210 in this manner. It should be appreciated that in this arrangement, the anchor extender 10 is readily disengageable from the anchor 210 as it is axially moved in a proximal direction relative to the anchor 210. However, the axial positioning of the anchor extender 10 relative to the anchor 210 may also be fixed upon further engagement of the anchor extender 10 with the anchor 210, further details of which will be provided below in connection with FIGS. 11-12A.

The anchor extender 10 can be further engaged with the anchor 210 by distally displacing the second member 18 relative to the first member 16. As the second member 18 is distally displaced, the transition portion 100 of the elongate passage 82 engages with the proximal end 218 of the receiver member 212 on the branches 222, 224 and guides the proximal end 218 into the second portion 98 of the elongate passage 82. The second member 218 is laterally displaced relative to the anchor 210 as the proximal end 218 is guided into the second portion 98 of the elongate passage 82, which in turn displaces the arms 28, 30 toward the first side 228 of the receiver member 212 such that the elongate tabs 46, 56 are moved into engagement with the lateral receptacles on the branches 222, 224 on the first side 228 of the receiver member 212. Once the elongated tabs are engaged with the branches 222, 224, the longitudinal axis L of the anchor extender 10 and the central axis 216 of the receiver member 212 are aligned with one another, as illustrated in FIG. 12A. In this arrangement, the anchor extender 10 is engaged with the anchor 210 such that it is not readily disengageable from the anchor 210 upon proximal movement of the anchor extender 10. Rather, in order to disengage the anchor extender 10 from the anchor 210 in this arrangement, the second member 18 is proximally displaced relative to the first member 16 to facilitate disengagement of the elongated tabs 46, 56 from the lateral receptacles of the branches 222, 224. While not previously discussed, it should be appreciated that while FIG. 12A illustrates engagement of the anchor extender 210 with the branch 222, engagement of the anchor extender 10 with the branch 224 will occur in the same manner.

Figure 11:
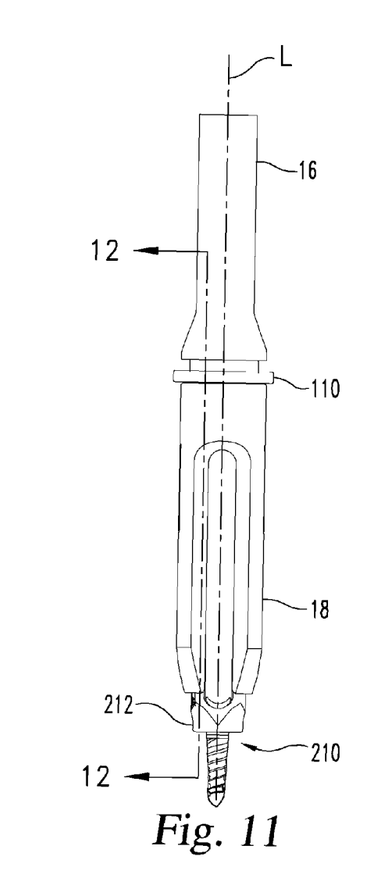
FIG. 11 is a side plan view of the anchor extender illustrated in FIG. 1 positioned in further engagement with the anchor.

In the arrangement illustrated in FIG. 12A, the distal ends 24, 74 of the first and second members 16, 18 are generally aligned with one another in a proximal/distal direction, and the elongate tabs 46, 56 are positioned in the elongate passage 82 opposite of and facing toward the transition portion 100 of the elongate passage 82. Moreover, the branch 222 is engaged on the first side 228 by the arm 28 of the first member 16 and on the second side 230 by the arm 78 of the second member 18, and the branch 224 is engaged on the first side 228 by the arm 30 of the first member 16 and on the second side 230 by the arm 80 of the second member 18. As illustrated in FIGS. 1, 8, and 11, the channel 226 is unobstructed by the first and second members 16, 18, and the slots 34, 86 of the first and second members 16, 18, respectively, align with one another and provide access to the channel 226. Similarly, the connecting element 240 may be guided along the slots 34, 86 into the channel 226. Further, as illustrated in FIG. 12, the elongate passages 32, 82 cooperate with one another to provide access through the anchor extender 10 to the channel 226 to facilitate engagement of a set screw with the internal threading 232 to lock the connecting element 240 in the channel 226.

Without limitation to any particular application, it is contemplated that the anchor extender 10 can be engaged with the anchor 210 to provide assistance in performing a variety of aspects associated with a surgical procedure, non-limiting examples of which include guiding and/or reducing the connecting element 240 into the channel 226 and/or facilitating rotation or manipulation of the anchor 210 to facilitate alignment of the channel 226 with the connecting element 240. Referring more particularly to FIG. 1, in the illustrated form, the reduction instrumentation 310 is coupled to the anchor extender 10 and configured to facilitate reduction of the connecting element 240 into the channel 226. While not illustrated in FIG. 1, it should be appreciated that the anchor extender 10 can be engaged with the anchor 210 in the manner discussed above in connection with FIG. 12A while the connecting element 240 is reduced into the channel 226.

The reduction instrumentation 310 generally includes a collar portion 312 positioned about the first member 16 and to which a release member 314 is pivotably coupled. The release member 314 generally includes an engaging portion (not shown) positioned in the elongate passage 32 of the first member 16 through the opening 36 and configured to engage with external threading of a reduction member 316. The reduction member 316 is rotatably coupled with a connecting element engaging portion 318 and, when engaged with the release member 314, distally advances or proximally withdraws the engaging portion 318 upon rotation in opposite directions relative to the anchor extender 10. The release member 314 is also generally configured to facilitate distal movement of the reduction member 316 relative to the anchor extender 10 without rotation of the reduction member 316 when it is engaged with the release member 314, and to prevent proximal movement of the reduction member 316 relative to the anchor extender 10 without rotation of the reduction member 316 when it is engaged with the release member 314. However, the release member 314 may also be displaced from engagement with the reduction member 316, in which case the reduction member 316 may be readily displaced relative to the anchor inserter 10 in both proximal and distal directions without rotation.

In operation, the reduction member 316 can be distally advanced, either by rotation, pushing without rotation, or a combination of the two, in order to seat the connecting element 240 in the channel 226. Once the connecting element 240 is seated in the channel 226, a set screw and related driver can be advanced through a hollow interior 320 of the reduction member 316 and engaged with the anchor 210 in order to secure the connecting element 240 in the channel 226. Once the connecting element 240 has been properly secured in the channel 226, the anchor extender 10 can be disengaged from the anchor 210 and removed, along with the reduction instrumentation 310, from the surgical site adjacent the anchor 210.

In addition to or in lieu of the foregoing, one or more instruments configured for adjusting, rotating or manipulating the position of the anchor 210 or the bone or bony tissue to which it is engaged may also be coupled with the anchor extender 10. Non-limiting examples of such instruments include those useful in derotating, compressing, distracting or otherwise adjusting the relative positioning of bones or bony tissues. Further, while not previously discussed, it should be appreciated that the anchor extender 10 can be engaged with the anchor 210 either before or after it has been engaged in bone or bony tissue. Similarly, in one form, the anchor extender 10 can be used during placement and engagement of the anchor 210 in the respective bone or bony tissue.

As indicated above, in one form, the anchor extender 10 can be used in connection with surgical procedures for stabilizing one or more segments of the spinal column. However, it should be appreciated that the use of the anchor extender 10 in other surgical procedures is also contemplated, including those performed in anatomical locations other than the spinal column. Additionally, the methods, techniques, assemblies, devices, apparatuses, systems and instrumentation described herein may also be used in surgical procedures involving animals, or in demonstrations for training, education, marketing, sales and/or advertising purposes. The methods, techniques, assemblies, devices, apparatuses, systems and instrumentation described herein may also be used on or in connection with a non-living subject such as a cadaver, training aid or model, or in connection with testing of surgical systems, surgical procedures, orthopedic devices and/or apparatus.

Any theory, mechanism of operation, proof, or finding stated herein is meant to further enhance understanding of the present application and is not intended to make the present application in any way dependent upon such theory, mechanism of operation, proof, or finding. It should be understood that while the use of the word preferable, preferably or preferred in the description above indicates that the feature so described may be more desirable, it nonetheless may not be necessary and embodiments lacking the same may be contemplated as within the scope of the application, that scope being defined by the claims that follow. In reading the claims it is intended that when words such as "a," "an," "at least one," "at least a portion" are used there is no intention to limit the claim to only one item unless specifically stated to the contrary in the claim. Further, when the language "at least a portion" and/or "a portion" is used the item may include a portion and/or the entire item unless specifically stated to the contrary.

While the application has been illustrated and described in detail in the drawings and foregoing description, the same is to be considered as illustrative and not restrictive in character, it being understood that only the selected embodiments have been shown and described and that all changes, modifications and equivalents that come within the spirit of the application as defined herein or by any of the following claims are desired to be protected.

The invention claimed is:

1. An apparatus, comprising:
an anchor including a bone engaging portion and a receiver member, said receiver member having a pair of oppositely positioned branches and a receiving channel positioned between said branches, said receiving channel extending between opposite first and second sides of said receiver member; and
an anchor extender engage able with said anchor, said anchor extender including:
a first member having an elongate body extending between a proximal end and an opposite distal end, said elongate body having oppositely positioned first and second arms each including an engaging portion structured to engage a respective one of said branches on said first side of said receiver member;
a second member positioned about said first member, said second member being movable relative to said first member between a first position and a second position and including a distal portion structured to engage with said branches on said second side of said receiver member; and
wherein distal movement of said second member relative to said first member from said first position to said second position moves said engaging portions of said first and second arms into engagement with said branches on said first side of said receiver member and said distal portion of said second member along said branches on said second side of said receiver member,
wherein said anchor extender includes a collar member rotatably coupled with said second member, said collar member including an alignment in structured to engage with a groove on said first member such that rotation of said collar member relative to said second member translates said second member relative to said first member.

2. The apparatus of claim 1, wherein said distal portion of said second member includes a distally opening receptacle configured to receive a portion of said branches of said receiver member, said receptacle including a first portion positioned distally of a second portion, said second portion including a reduced cross-sectional dimension relative to said first portion.

3. The apparatus of claim 2, wherein said distal portion of said second member further includes a ramped surface extending between said first and second portions of said receptacle, said ramped surface being structured to engage with and position said portion of said branches from said first portion to said second portion of said receptacle as said second member is moved distally to said second position.

4. The apparatus of claim 3, wherein said branches of said receiver member are positioned between said ramped surface and said first and second arms of said first member when said anchor extender is engaged with said anchor.

5. The apparatus of claim 3, wherein each of said engagement portions of said first and second arms is engaged with said respective one of said branches on said first side when said portion of said branches is positioned in said second portion of said receptacle.

6. The apparatus of claim 3, wherein said first and second arms of said first member are positioned in said receptacle opposite of said ramped surface.

7. The apparatus of claim 1, wherein said first member extends along a longitudinal axis between said proximal and distal ends and each of said engaging portions of said first and second arms includes an elongated tab, each of said elongated tabs being offset from said longitudinal axis and extending substantially parallel to one another from said first and second arms.

8. The apparatus of claim 7, wherein each of said elongated tabs is positioned in a corresponding recess in said first and second arms, said recesses cooperating to define a socket for receiving a portion of said branches on said first side of said receiver member when said second member is in said first and second positions.

9. The apparatus of claim 1, wherein said first member includes a first elongated slot positioned between said first and second arms, said second member includes a second elongated slot, and said first and second elongated slots are aligned with one another and define a passage extending substantially parallel to said receiving channel.

10. The apparatus of claim 1, wherein said first member further includes a proximal portion from which said first and second arms extend, said proximal portion including an elongate hollow interior and a distal facing surface extending thereabout, said distal facing surface limiting proximal movement of said second member relative to said first member.

11. The apparatus of claim 1, wherein said first member includes a pair of longitudinal tongues positioned on said first and second arms, said tongues being configured to engage a respective one of oppositely positioned longitudinal grooves formed along an inner surface of said second member.

12. The apparatus of claim 1, wherein said anchor extender is coupled with said anchor in an axially fixed relationship when said second member is in said second position.

13. An anchor extender, comprising:
a first member including a first elongate body extending along a first longitudinal axis between a proximal end and an opposite distal end, said first elongate body having a pair of oppositely positioned tabs laterally offset from and extending toward said first longitudinal axis;
a second member including a second elongate body extending along a second longitudinal axis between a proximal end and an opposite distal end, said second elongate body having an elongate passage extending between said proximal and distal ends, said elongate passage having a first portion positioned adjacent said distal end, a second portion positioned proximally of said first portion, and a transition portion extending obliquely toward said second longitudinal axis in a proximal direction from said first portion to said second portion of said elongate passage;
a collar member rotatably coupled with said second member, said collar member including an alignment pin structured to engage with a groove on said first member such that rotation of said collar member relative to said second member translates said second member relative to said first member; and
wherein said second member is positionable over said first member and slidably movable relative to said first member across a plurality of positions, said plurality of positions including an anchor engaging position in which said oppositely positioned tabs are positioned in said elongate passage opposite of and facing said transition portion of said elongate passage.

14. The anchor extender of claim 13, wherein said first elongate body includes a first arm laterally spaced from a second arm, and a respective one of said pair of tabs is positioned on each of said first and second arms.

15. The anchor extender of claim 14, wherein each of said tabs is positioned in a corresponding recess on said first and second arms.

16. The anchor extender of claim 13, wherein said first elongate body of said first member includes a proximal portion from which said first and second arms extend, said proximal portion having an elongate hollow interior extending coaxially with said elongated passage of said second member.

17. A method, comprising:
providing an anchor including a bone engaging portion and a receiver member, the receiver member extending along a central axis between a proximal end and an oppositely positioned distal end and further including a pair of oppositely positioned branches and a receiving channel positioned between the branches, the receiving channel extending between opposite first and second sides of the receiver member;
providing an anchor extender engageable with the anchor, the anchor extender extending along a longitudinal axis between a proximal end and an opposite distal end and including:
a first member including oppositely positioned first and second arms each having an engaging portion structured to engage a respective one of the branches on the first side of the receiver member;
a second member movably positioned about the first member and including a distal portion structured to engage the branches on the second side of the receiver member;
positioning the anchor extender adjacent the proximal end of the receiver member with the longitudinal axis of the anchor extender offset from the central axis of the receiver member; and
distally moving the second member relative to the first member to releasably couple the anchor extender with the receiver member, the moving including aligning the longitudinal axis with the central axis.

18. The method of claim 17, wherein distally moving the second member includes engaging the engaging portions of the first and second arms with the branches on the first side of the receiver member.

19. The method of claim 18, wherein distally moving the second member includes engaging the distal portion of the second member with the branches on the second side of the receiver member.

* * * * *